(12) United States Patent
Vishnubholta et al.

(10) Patent No.: US 8,979,933 B2
(45) Date of Patent: Mar. 17, 2015

(54) STAND-ALONE INTERBODY FIXATION SYSTEM

(71) Applicant: Alphatec Spine, Inc., Carlsbad, CA (US)

(72) Inventors: Sri Vishnubholta, Carlsbad, CA (US); Yang Cheng, Carlsbad, CA (US); Leopoldo Castillo, Carlsbad, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 32 days.

(21) Appl. No.: 13/633,301

(22) Filed: Oct. 2, 2012

(65) Prior Publication Data

US 2014/0094918 A1    Apr. 3, 2014

Related U.S. Application Data

(63) Continuation-in-part of application No. 12/852,033, filed on Aug. 6, 2010, now Pat. No. 8,328,870.

(60) Provisional application No. 61/231,967, filed on Aug. 6, 2009.

(51) Int. Cl.
*A61F 2/44* (2006.01)
*A61F 2/30* (2006.01)

(52) U.S. Cl.
CPC ............. *A61F 2/442* (2013.01); *A61F 2/4455* (2013.01); *A61F 2002/30476* (2013.01); *A61F 2002/3052* (2013.01); *A61F 2002/30579* (2013.01)
USPC ...................... 623/17.16; 623/17.11

(58) Field of Classification Search
CPC ............ A61B 17/70; A61B 17/1671; A61B 17/7067; A61B 17/1757; A61B 2017/0256; A61B 17/809; A61F 2/44; A61F 2/4455; A61F 2310/00023; A61F 2/4611; A61F 2002/30841; A61F 2002/30904; A61F 2002/448
USPC ............................... 623/17.11–17.16
See application file for complete search history.

(56) References Cited

U.S. PATENT DOCUMENTS 5,683,394 A * 11/1997 Rinner .................. 606/86 R
2006/0293673 A1 * 12/2006 Morrison et al. ............ 606/69

* cited by examiner

*Primary Examiner* — Mary Hoffman
*Assistant Examiner* — Tara R Carter
(74) *Attorney, Agent, or Firm* — Michael J Loi

(57) ABSTRACT

A stand-alone interbody fixation system having a cage, anterior fixation blade and posterior fixation blade. The cage includes an annular side wall with an open interior and upper and lower surfaces, the cage being configured to fit between end plates of adjacent vertebrae. The anterior fixation blade includes an anterior alignment boss with two opposing outward extending anterior blades with end plate penetrating tips configured to fit within the open interior of the cage. The posterior fixation blade includes a posterior alignment boss with two opposing outward extending posterior blades with end plate penetrating tips configured to fit within the open interior of the cage. The anterior and posterior fixation blades are counter-rotating blades and the anterior alignment boss and posterior alignment boss are configured to receive or engage a deployment instrument having an anterior engagement portion and a posterior engagement portion configured to rotate the anterior and posterior fixation blades from a stowed position to a deployed condition.

19 Claims, 12 Drawing Sheets

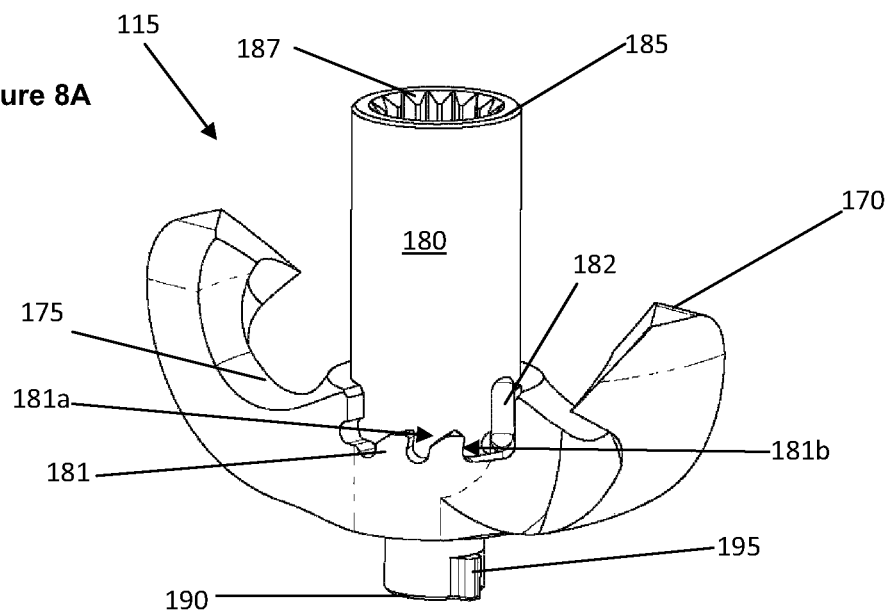
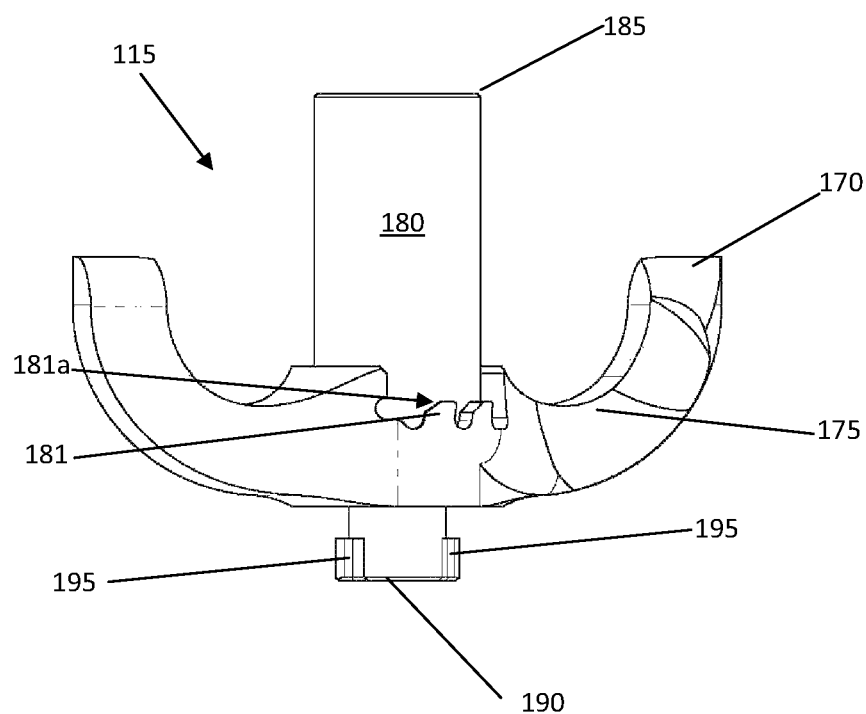

STAND-ALONE INTERBODY FIXATION SYSTEM

CROSS-REFERENCES TO RELATED APPLICATIONS

The present application is a continuation-in-part of U.S. patent application Ser. No. 12/852,033, filed Aug. 6, 2010, which claims priority from U.S. Provisional Application No. 61/231,967, which was filed on Aug. 6, 2009, both of which are incorporated herein by reference in their entirety.

BACKGROUND

The present invention generally relates to the field of spinal orthopedics, and more particularly to methods and systems for securing interbody cages within the intervertebral space.

The spine is a flexible column formed of a plurality of bones called vertebra. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies.

The intervertebral fibro-cartilages are also known as inter-vertebral disks and are made of a fibrous ring filled with pulpy material. The disks function as spinal shock absorbers and also cooperate with synovial joints to facilitate movement and maintain flexibility of the spine. When one or more disks degenerate through accident or disease, nerves passing near the affected area may be compressed and are consequently irritated. The result may be chronic and/or debilitating back pain. Various methods and apparatus have been designed to relieve such back pain, including spinal fusion using an interbody spacer or suitable graft using techniques such as Anterior Lumbar Interbody Fusion (ALIF), Posterior Lumbar Interbody Fusion (PLIF), or Transforaminal Lumbar Interbody Fusion (TLIF) surgical techniques. The implants used in-these techniques, also commonly referred to as vertebral body replacements (VBR) devices, are placed in the interdiscal space between adjacent vertebrae of the spine. Many times an exterior plate is used in conjunction with the VBR to hold the adjacent vertebrae while the fusion occurs.

Ideally, the interbody spacer should stabilize the intervertebral space and allow fusion of the adjacent vertebrae. Moreover, during the time it takes for fusion to occur, the interbody spacer should have sufficient structural integrity to withstand the stress of maintaining the space without substantially degrading or deforming and have sufficient stability to remain securely in place prior to actual bone ingrowth fusion.

One significant challenge to providing fusion stability (prior to actual bone ingrowth fusion) is preventing spinal extension during patient movement. Distraction of the vertebral space containing the fusion graft may cause the interbody spacer to shift or move disrupting bone ingrowth fusion and causing pain. An exterior plate is often used with the interbody spacer to hold the adjacent vertebrae while the fusion occurs.

There remains a need for an interbody spacer capable of holding the adjacent vertebrae steady during fusion without the use of external plates.

SUMMARY OF THE INVENTION

Generally, embodiments of the present invention provide a stand-alone single fixation system having a cage, an anterior fixation blade and a posterior fixation blade. The anterior and posterior blades may be positioned within the cage in a delivery position and rotated from the cage to a deployed position. A ratcheting mechanism is provided which engages with the blades to lock the blades in position as they are deployed. The stand-alone interbody fixation system is a pre-assembled multi-component design which integrates a fixation feature with an interbody spacer, no additional support is required. The system may be used in spinal fusion surgeries including ALIF, PLIF and TLIF procedures, wherein two or more vertebrae are joined or fused together for the treatment of spinal disorders such as spondylolisthesis, scoliosis, severe disc degeneration, or spinal fractures. The system may also be used in open and minimally invasive surgery (MIS) procedures, and using low profile instrumentation facilitates a less invasive approach through a smaller incision.

In a first aspect, embodiments of the present invention provide a stand-alone interbody fixation system having a cage, anterior fixation blade and posterior fixation blade. The cage includes an annular side wall with an open interior and upper and lower surfaces, the cage being configured to fit between end plates of adjacent vertebrae. The anterior fixation blade includes an anterior alignment boss with two opposing outward extending anterior blades with end plate penetrating tips configured to fit within the open interior of the cage, the anterior alignment boss having first and second ends, the first end of the anterior alignment boss being rotatably coupled with a first opening in the annular side wall. The posterior fixation blade includes a posterior alignment boss with two opposing outward extending posterior blades with end plate penetrating tips configured to fit within the open interior of the cage, the posterior alignment boss having first and second ends, the first end being rotatably coupled to the second end of the anterior alignment boss and the second end of the posterior alignment boss being rotatably coupled with a second opening in the annular side wall opposite the first opening. A C-clip, having ratchet pawls, is disposed so as to maintain the engagement between the alignment bosses and the cage. The anterior and posterior alignment bosses further comprise ratchet teeth configured to engage with the ratchet pawls on the C-clip used to keep the anterior and posterior fixation blades in the fixation blade retention position in the cage. There is a tactile and audible feedback to the user when the pawl jumps over the ratchet teeth on the blades. The anterior and posterior fixation blades are counter-rotating blades and the anterior alignment boss and posterior alignment boss are configured to receive or engage a deployment instrument having an anterior engagement portion and a posterior engagement portion configured to rotate the anterior and posterior fixation blades from a stowed position to a deployed condition.

In many embodiments, the anterior and posterior alignment bosses may further include fine spline features configured to receive or engage the deployment instrument.

In many embodiments, the C-clip further includes slot springs, which enhance the ease with which the ratchet pawls can engage the ratchet teeth features on the anterior and posterior fixation blades.

In many embodiments, the anterior and posterior alignment bosses, as well as the C-clip, may further include dovetail features designed to retain the C-clip, and prevent the C-clip from disengaging from the system if the blades are over deployed.

In another embodiment, the C-clip may serve to limit the final angulation between the blades.

In many embodiments, the cage further includes a blade stop to prevent the blades from exceeding maximum deployment.

In many embodiments, the anterior and posterior blades further include a cutting edge between the boss and tip.

In many embodiments, the anterior and posterior blades are curved blades. The curved blades may be shaped to follow the annular side wall within the open interior.

In many embodiments, the anterior and posterior blades may be constructed of titanium, a titanium alloy, polyetherketoneketone (PEEK), or any other biologically acceptable materials, or a combination of the materials, capable of penetrating the end plate.

In many embodiments, the anterior engagement portion of the deployment instrument is configured to engage the first end of the anterior alignment boss and the posterior engagement portion is configured to engage the first end of the posterior alignment boss through an opening in the anterior alignment boss.

In many embodiments, when coupled, the anterior and posterior fixation blades are movable from a fixation blade insertion position for positioning the coupled anterior and posterior blades in the cage to a fixation blade retention position in which the coupled anterior and posterior fixation blades are moved apart and the first end of the anterior alignment boss is within the first opening in the annular side wall and the second end of the posterior alignment boss is within the second opening in the annular side wall. The C-clip may be used to keep the anterior and posterior fixation blades in the fixation blade retention position in the cage. In addition, the ratchet teeth on the bosses and the ratchet pawls on the C-clip provide a locking feature to prevent collapse of the blades as they are deployed, enabling the blades to lock in partially deployed positions between the stowed and fully deployed positions. There is a tactile and audible feedback to the user when the pawl jumps over the ratchet teeth on the blades.

In many embodiments, the first and second openings in the annular side wall include grooves and the first end of the anterior boss and the second end of the posterior boss include bumps, the bumps configured to interact with the grooves and hold the anterior and posterior fixation blades in one or more positions.

In many embodiments, the upper and lower surfaces include outwardly projecting sharp raised ridges, teeth and/or striations.

In another aspect, embodiments of the present invention provide a stand-alone interbody fixation system having a cage with an annular side wall with an open interior and upper and lower surfaces having outwardly projecting sharp raised ridges, teeth and/or striations, the cage being configured to fit between end plates of adjacent vertebrae, an anterior fixation blade having an anterior alignment boss with two curved opposing outward extending anterior blades shaped to follow the annular side wall within the open interior, the blades being capable of penetrating the end plate, the anterior alignment boss being rotatably coupled to a first opening in the annular side wall, and a posterior fixation blade having a posterior alignment boss with two curved opposing outward extending posterior blades shaped to follow the annular side wall within the open interior, the blades being capable of penetrating the end plate, the posterior alignment boss being rotatably coupled to the anterior alignment boss and further rotatably coupled with a second opening in the annular side wall opposite the first opening. A C-clip, having ratchet pawls, is disposed so as to maintain the engagement between the alignment bosses and the cage. The anterior and posterior alignment bosses further comprise ratchet teeth configured to engage with the ratchet pawls on the C-clip used to keep the anterior and posterior fixation blades in the fixation blade retention position in the cage. There is a tactile and audible feedback to the user when the pawl jumps over the ratchet teeth on the blades. The anterior and posterior fixation blades are counter-rotating blades and the anterior alignment boss and posterior alignment boss are configured to receive or engage a deployment instrument having an anterior engagement portion and a posterior engagement portion configured to rotate the anterior and posterior fixation blades from a stowed position to a deployed condition. The anterior and posterior fixation blades are counter-rotating blades and are configured to receive or engage a counter-rotating deployment instrument configured to counter-rotate the anterior and posterior fixation blades from a stowed position to a deployed condition.

In many embodiments, the anterior and posterior blades further include end plate penetrating tips.

In many embodiments, the deployment instrument includes an anterior engagement portion configured to engage the anterior alignment boss and a posterior engagement portion configured to engage the posterior alignment boss.

In many embodiments, the first and second openings in the annular side wall include grooves and the anterior alignment boss and the posterior alignment boss include bumps, the bumps configured to interact with the grooves and hold the anterior and posterior fixation blades in one or more positions.

In many embodiments, the C-clip further includes slot springs, which enhance the ease with which the ratchet pawls can engage the ratchet teeth features on the anterior and posterior fixation blades.

In many embodiments, the anterior and posterior alignment bosses, as well as the C-clip, may further include dovetail features designed to retain the C-clip, and prevent the C-clip from disengaging from the system if the blades are over deployed.

In many embodiments, the anterior and posterior alignment bosses may further include fine spline features configured to receive or engage the deployment instrument.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

FIGS. 8A-E show different views of one embodiment of a posterior fixation blade having a ratchet teeth locking feature.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

Figure 1A:
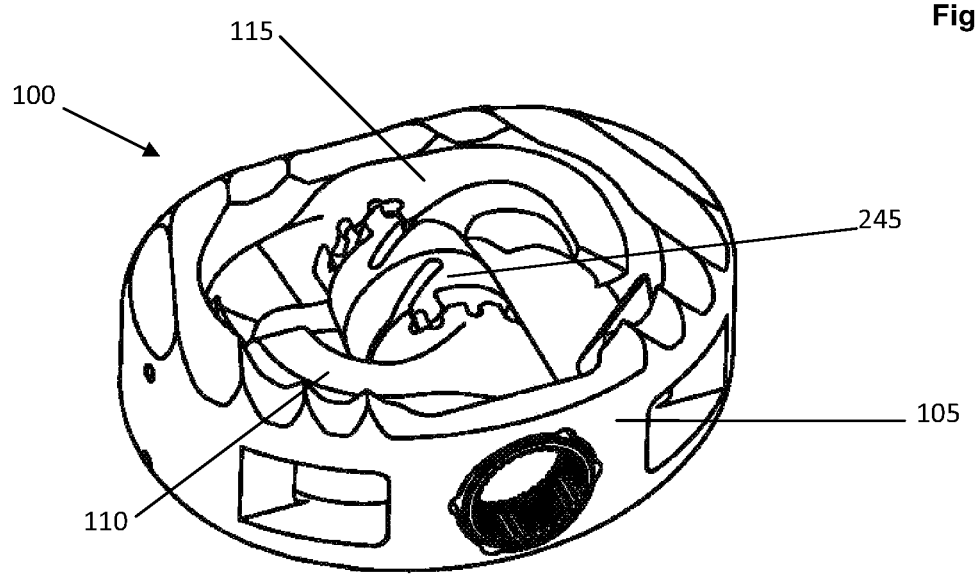
FIG. 1A shows a perspective view of one embodiment of a stand-alone interbody fixation system having a ratchet teeth locking feature, wherein blades are in a delivery position.
Figure 1B:
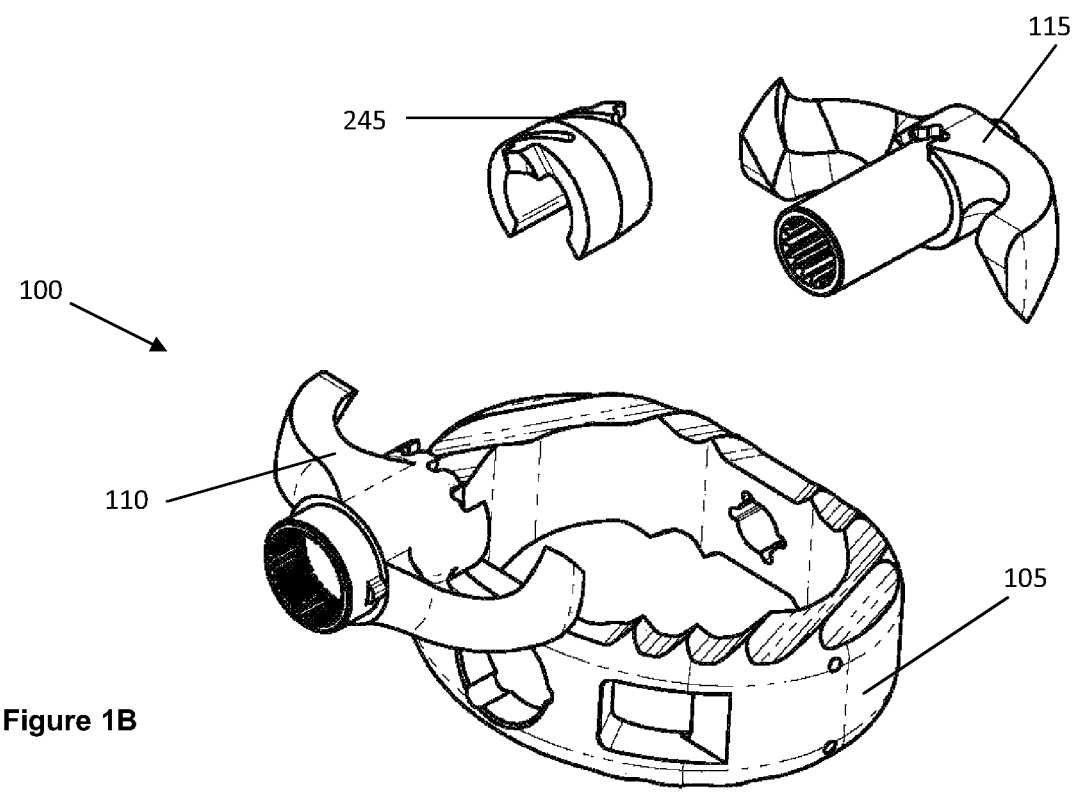
FIG. 1B shows an exploded view of one embodiment of a stand-alone interbody fixation system having a ratchet teeth locking feature.
Figure 2:
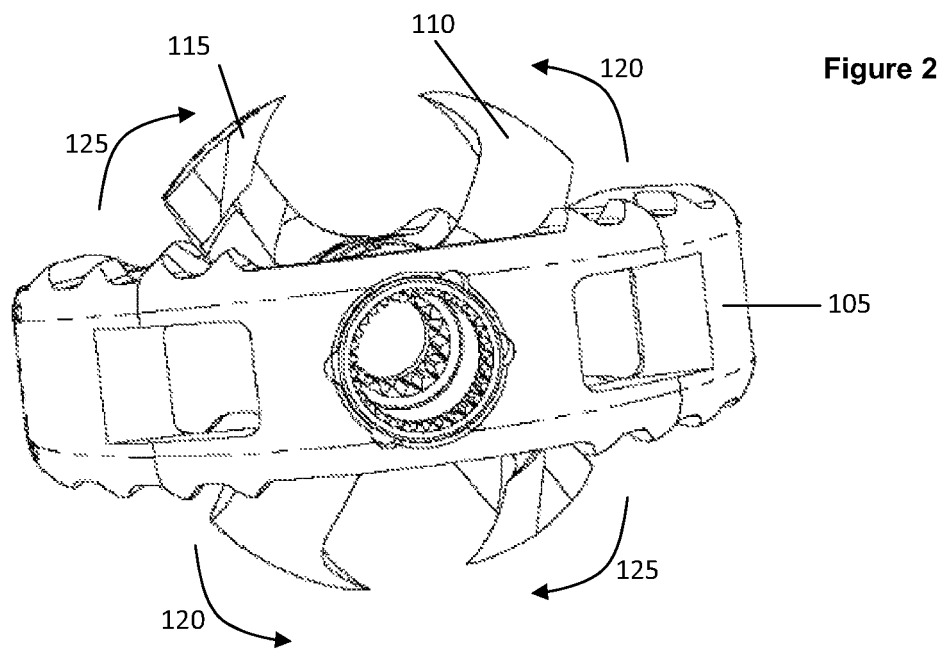
FIG. 2 shows a perspective view of one embodiment of a stand-alone interbody fixation system having a ratchet teeth locking feature, wherein blades are in a deployed position.

FIGS. 1a-b and 2 illustrate schematically one embodiment of a stand-alone interbody fixation system 100. The stand-alone interbody fixation system 100 is a pre-assembled multi-component design which integrates a fixation feature with an interbody spacer with no additional support required. In preferred embodiments, the system 100 is used in spinal fusion surgeries including, but not limited to Anterior Lumbar Interbody Fusion (ALIF), Posterior Lumbar Interbody Fusion (PLIF), or Transforaminal Lumbar Interbody Fusion (TLIF), lateral and cervical procedures, wherein two or more vertebrae are joined or fused together for the treatment of spinal disorders such as spondylolisthesis, scoliosis, severe disc degeneration, or spinal fractures. While the embodiments are described primarily in the context of an ALIF procedure, use with other procedures are also contemplated. The system 100 may be used in a variety of spinal procedures, including open procedures and minimally invasive surgery (MIS) procedures using low profile instrumentation which facilitates a less invasive approach through a smaller incision. As can be understood by one skilled in the art, these embodiments are shown for illustrative purposes and are not intended to limit the scope of the invention.

The unique design of the stand-alone interbody fixation system 100 provides a solid fixation in all aspects (flexion, extension, torsion, rotation, migration). In many embodiments, the system 100 is configured to use a single instrument to distract, insert and deploy the system. The design allows for multiple footprint shapes, ranging from 20-40 mm in both length and width to ensure adequate contact with cortical rim. In many embodiments, the design includes a tapered leading portion that allows smooth insertion and deployment. The height may range from 8-20 mm, but other heights are also contemplated, depending on location. Lordosis ranging from 0-20 degrees to accommodate surgical needs.

The system 100 disclosed uses counter rotating blades 110, 115 that provide 4 points of fixation with 2-10 mm of blade engagement. In order to maintain bone purchase or blade engagement for each implant height and footprint, the blade length may be increased or decreased to accommodate the cage height. As the blade rotates from its resting position to the deployed position, the amount of exposed blade is controlled across the various implant sizes. While counter rotating blades are disclosed, other embodiments may deploy the blades rotating in the same direction. Ratcheting features provide locking features to lock the blades while fully or partially deployed. A C-clip 245 serves to hold the blades 110, 115 in position within the cage 105 and provide secure deployment and engagement of blades with positive feedback when blades are deployed and locked. An internal lock prevents accidental deployment and positive tangible feedback to a surgeon when the blades are fully deployed. The blades are securely held in place and some embodiments may include elements to prevent over-deployment. In some embodiments, the ability to reverse deployment and remove or reposition implant may be desirable. The unique blade shape allows adequate space to pack bone graft before insertion. There are also access ports in the interbody spacer or cage to allow additional bone graft to be added after insertion/deployment. Some embodiments of the blade shape geometry may also pull the endplates together when deployed. In another embodiment, the C-clip 245 may serve to limit the final angulation between the blades.

Figure 3:
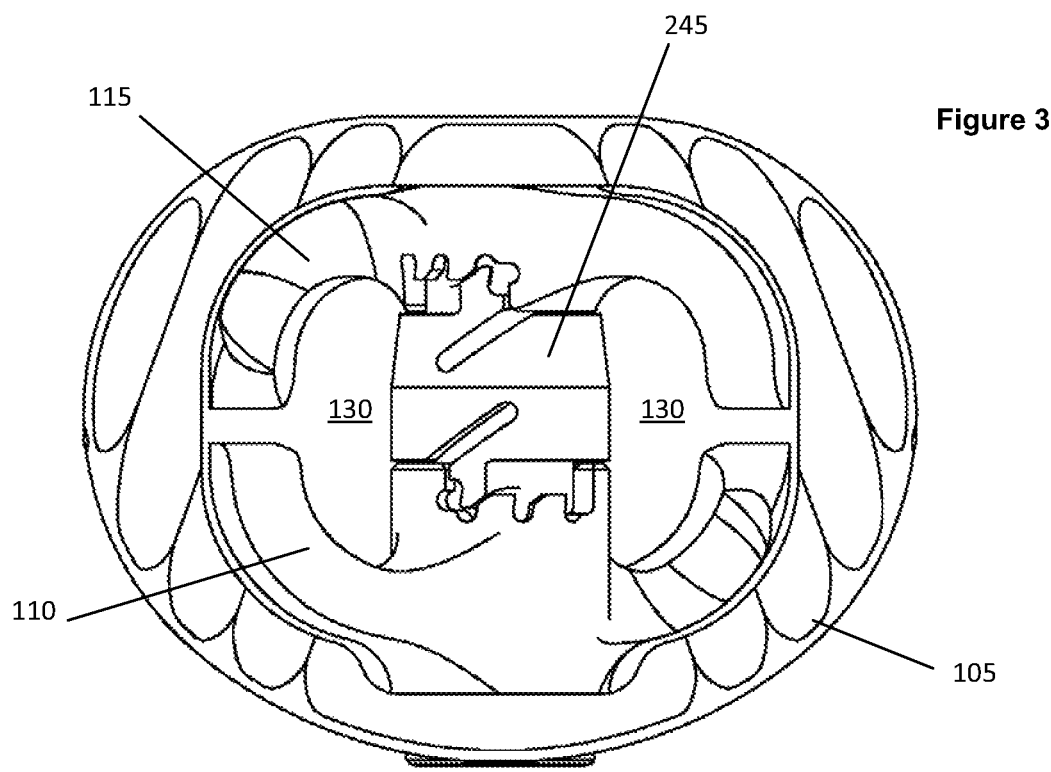
FIG. 3 shows a top view of the embodiment of a stand-alone interbody fixation system having a ratchet teeth locking feature shown in FIG. 1A.
Figure 4:
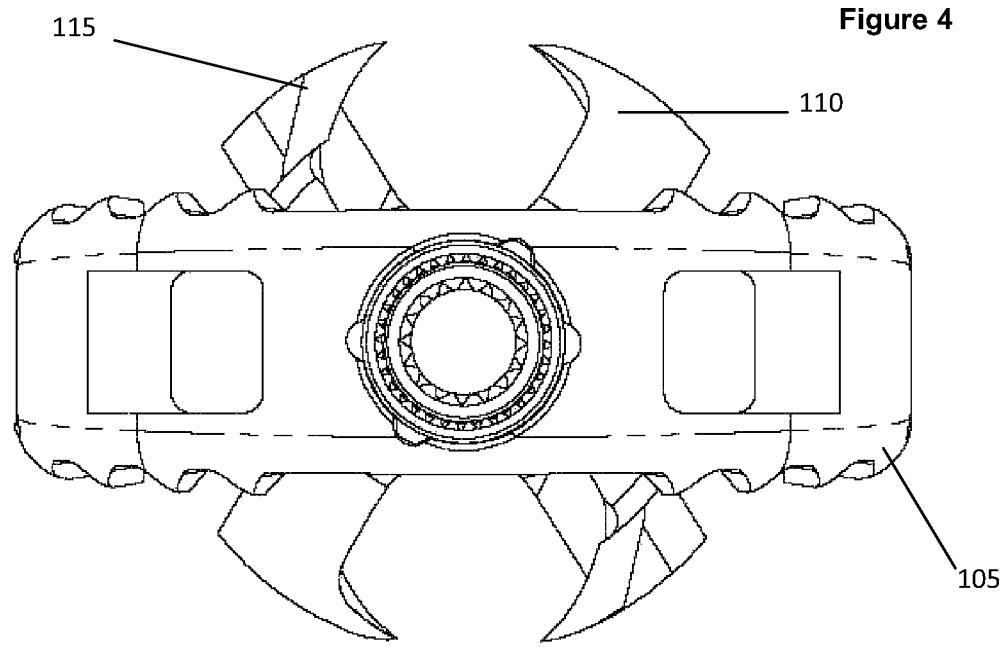
FIG. 4 shows a posterior view of the embodiment of a stand-alone interbody fixation system having a ratchet teeth locking feature shown in FIG. 2.
Figure 5A:
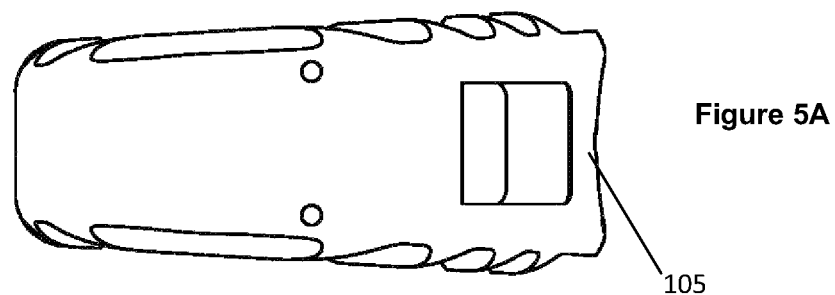
FIG. 5A shows a side view of the cage of the embodiment of a stand-alone interbody fixation system having a ratchet teeth locking feature shown in FIG. 1A.
Figure 5B:
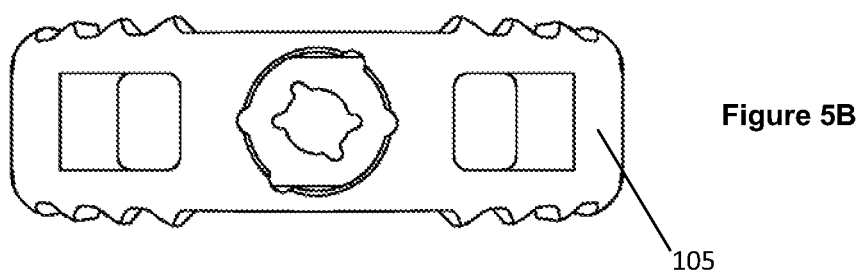
FIG. 5B shows a front view of the cage of the embodiment of a stand-alone interbody fixation system having a ratchet teeth locking feature shown in FIG. 1A.

The stand-alone interbody fixation system 100 includes a cage 105, an anterior fixation blade 110 and a posterior fixation blade 115. FIG. 1a is a perspective view showing the anterior 110 and posterior 115 blades within the cage 105 in a delivery position, where the C-clip 245 holds the blades 110, 115 in an engaged position with the cage 105. FIG. 1b is an exploded view of the fixation system 100 of FIG. 1a. FIG. 2 is a perspective view showing the anterior 110 and posterior 115 blades in the deployed position. FIG. 3 is a top view showing an embodiment in which the curved anterior 110 and posterior 115 blades are designed to follow shape of the interior of the cage 105 resulting in axial windows 130 that may be used for packing of bone graft material, or other types of bone growth materials or biologics (not shown), within to expedite the fusion of the cage in the spinal column. FIG. 4 is a view looking posteriorly showing the cage 105 and the anterior 110 and posterior 115 blades in the deployed position. FIG. 5A is a side view and FIG. 5B is a front view of the cage 105 and the anterior 110 and posterior 115 blades in the stowed position. As shown in FIGS. 5A and 5B, when the anterior 110 and posterior 115 blades in the stowed or rest position they are under the boundaries or surfaces of the cage 105 geometry. This allows the system 100 to be inserted between the end plates of adjacent vertebrae without anterior 110 and posterior 115 blades contacting the end plates.

In an ALIF procedure, the stand-alone interbody fixation system 100 is inserted and fixated from an anterior approach so that posterior muscular structures are preserved and surgical morbidity associated with 360° surgical techniques is eliminated. Once inserted, the anterior fixation blade 110 rotates in a clockwise rotation 120 and the posterior fixation blade 115 rotates in a counterclockwise rotation 125, shown in FIG. 2, biting into the vertebral end plates (not shown). As the blades rotate, the ratchet teeth features disposed on the anterior blade 110 and posterior blade 115 engage with the ratchet pawl features disposed on the C-clip 245, locking the blades in partially or fully deployed states. There is a tactile and audible feedback to the user when the pawl jumps over the ratchet teeth on the blades. While embodiments below are described primarily in the context of two counter rotating blades, other number of blades and rotations are also contemplated.

Figure 6A:
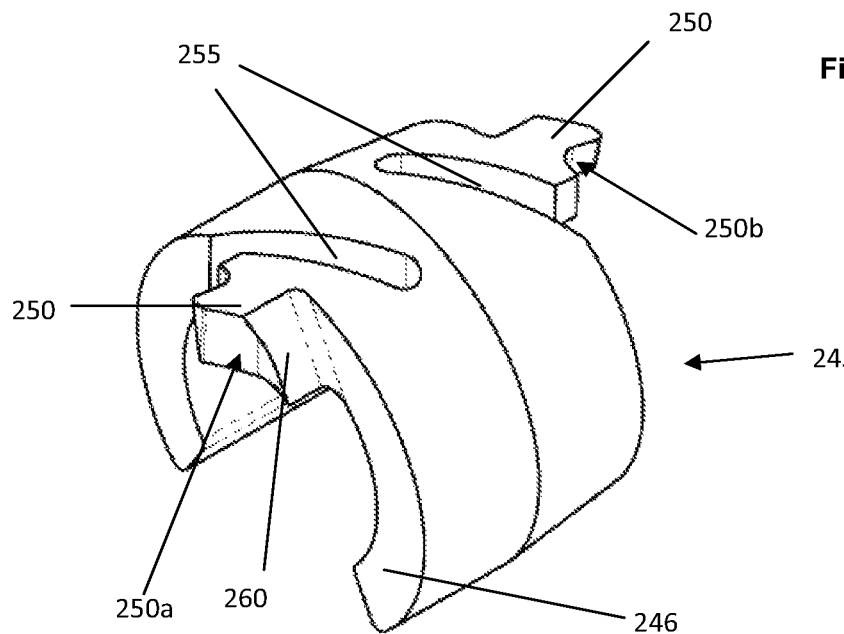
FIGS. 6A-B show different views of one embodiment of a C-clip having ratchet pawl locking features.
Figure 6B:
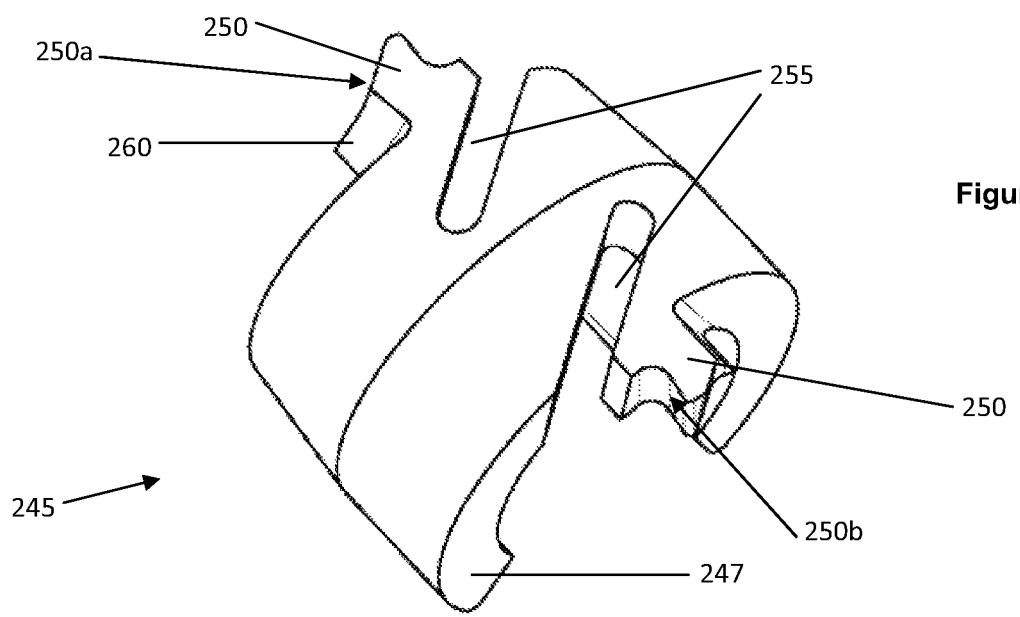

FIGS. 6A-B show different views of one embodiment of a C-clip 245 adapted for use with the system 100. The C-clip 245 has a first side 246 and a second side 247, each side 246, 247 adapted to engage with either the anterior blade 110 or the posterior blade 115. Each side 246, 247 further includes ratchet pawl features 250. In one embodiment, the ratchet pawls 250 have a 25 degree engagement angle 250a and a 10 degree back angle 250b. The back angle 250b prevents the ratchet pawls 250 from disengaging the blades 110, 115, which would permit the blades 110, 115 to collapse and back out from a deployed position. In many embodiments, each side 246, 247 of the C-clip 245 further includes a slot spring 255, which enhances the ease with which the ratchet pawls 250 can engage ratchet teeth features on the blades 110, 115. In some embodiments, the sides 246, 247 of the C-clip 245 may also include dovetail features 260. The dovetail features 260 are designed to contact receiving dovetail features on the blades 110, 115, so as to retain the C-clip 245 in position and prevent the C-clip 245 from "popping out" or otherwise disengaging from the system 100 in the event that the blades 110, 115 are over deployed. In another embodiment, the C-clip 245 may serve to limit the final angulation between the blades 110, 115.

Figure 7A:
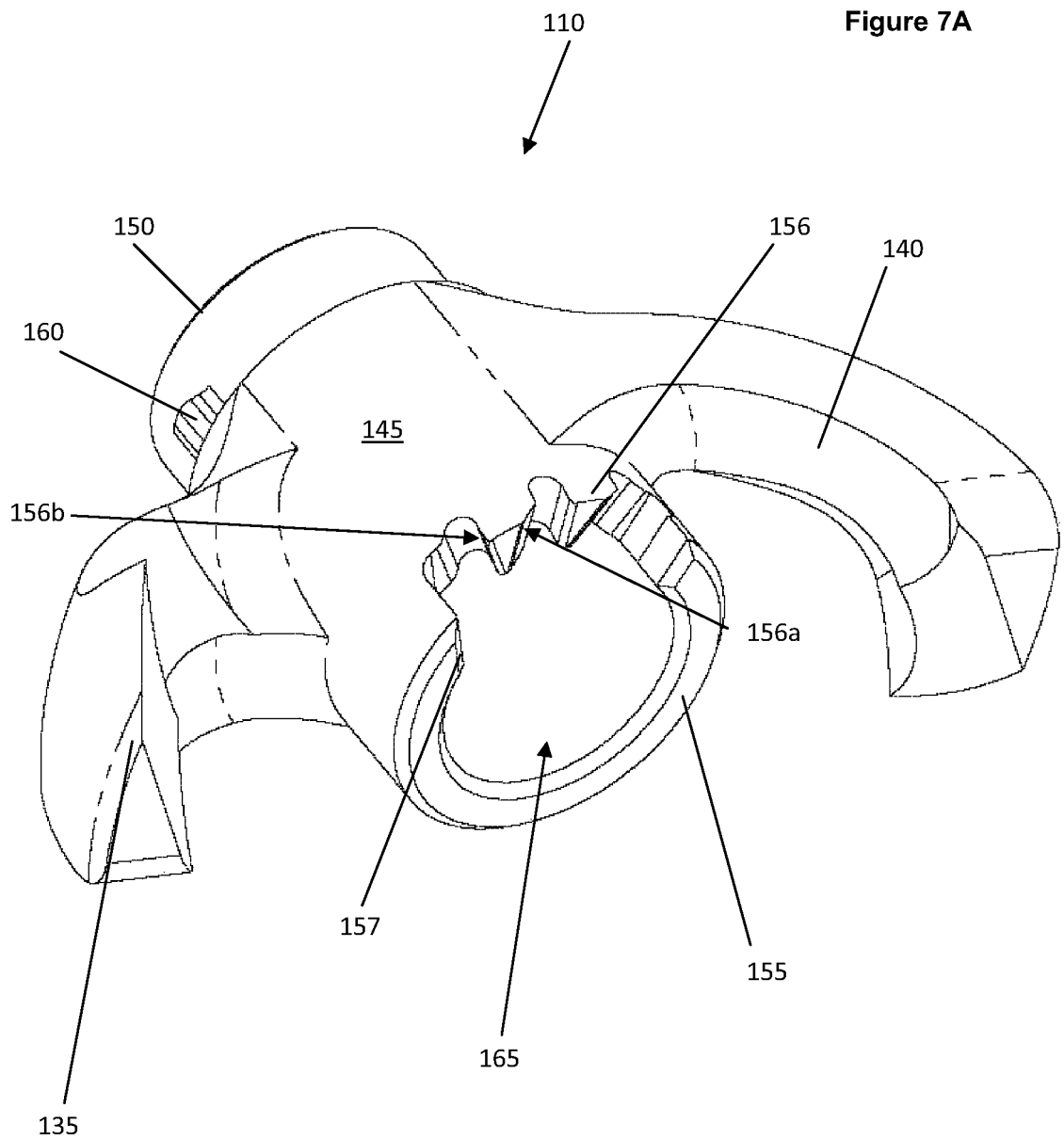
FIGS. 7A-C show different views of one embodiment of an anterior fixation blade having a ratchet teeth locking feature.
Figure 7B:
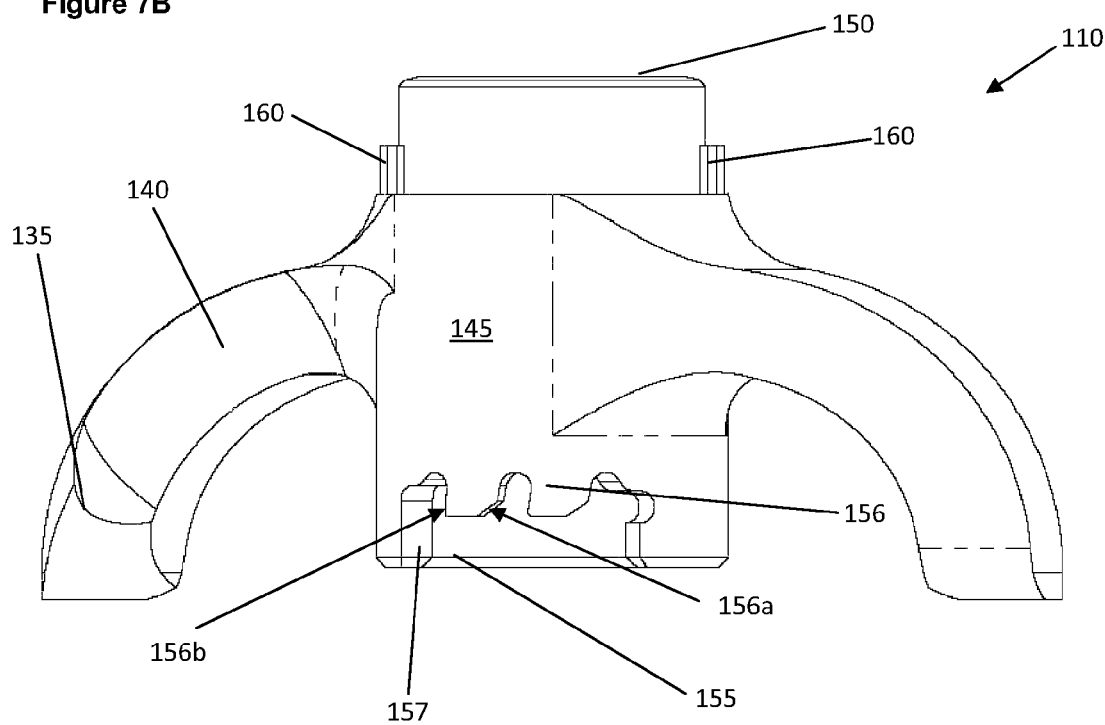
Figure 7C:
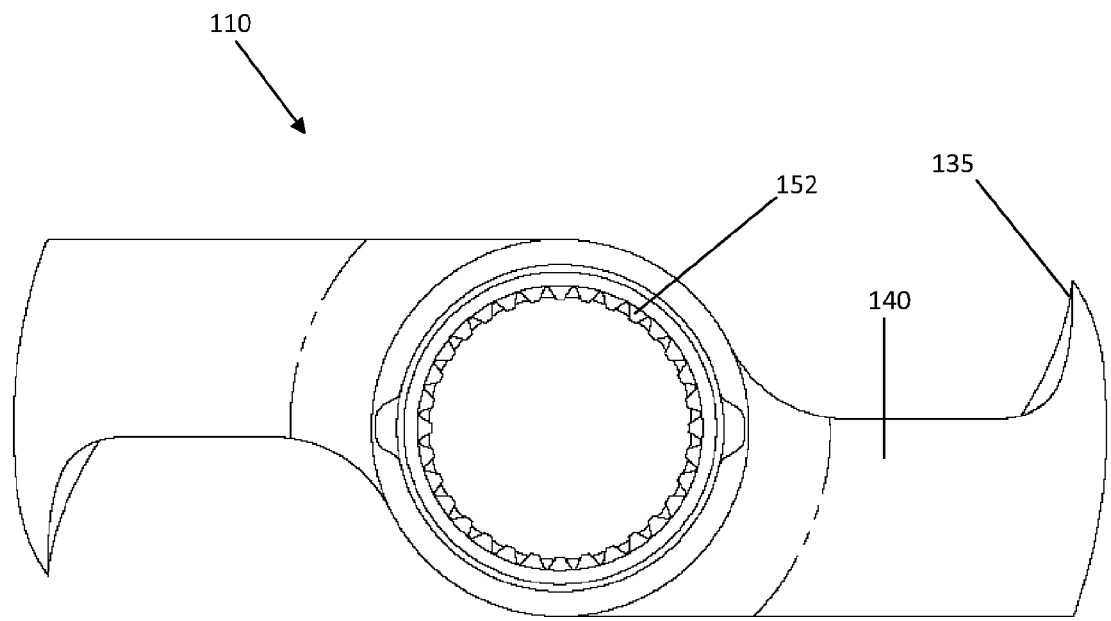
Figure 8C:
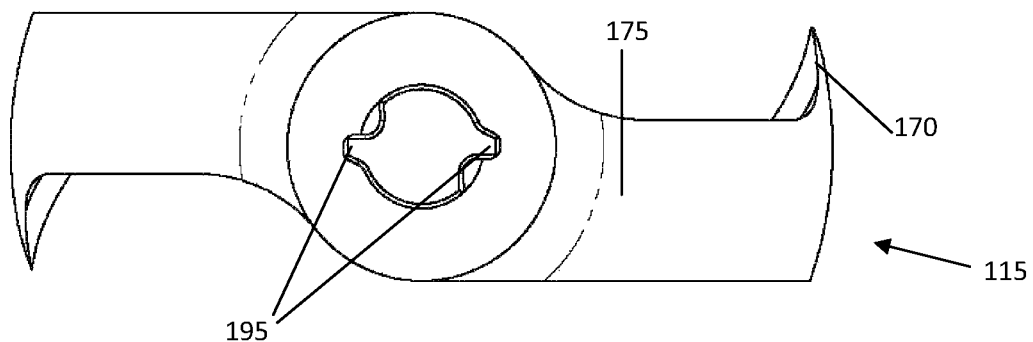
Figure 8D:
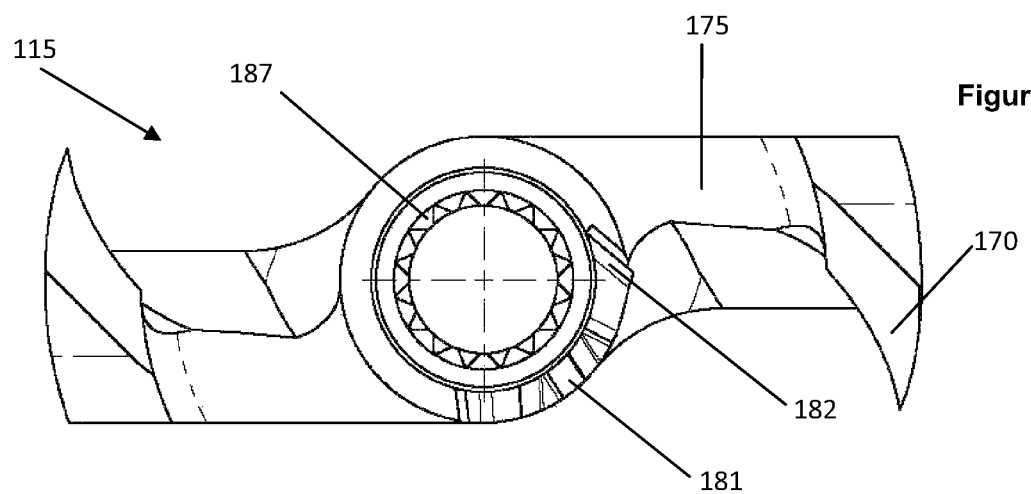
Figure 8E:
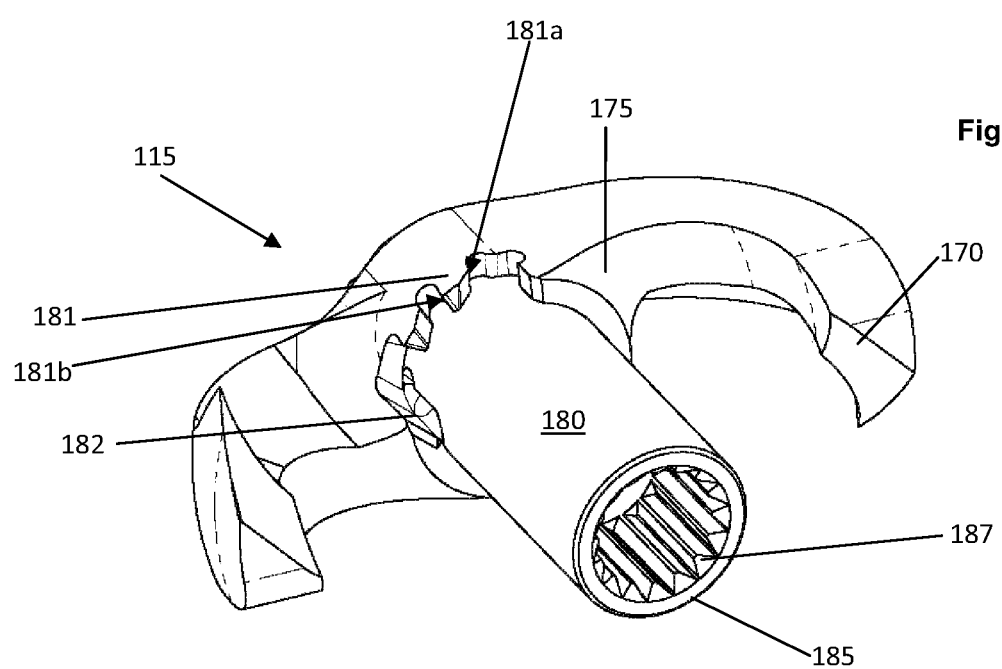

FIGS. 7A-7C show one embodiment of an anterior fixation blade 110 that includes curved blades designed to penetrate the end plates of adjacent vertebrae. The curved blades may have a smooth curve or may be a series of straight sections. Using curved blades maximizes graft volume and minimizes graft displacement during deployment. The anterior fixation blade 110 may be constructed of titanium, a titanium alloy, polyetherketoneketone (PEEK), or any other biologically acceptable materials that would engage the spine plate and provide a rigid structure. The anterior fixation blade 110 may be constructed using one material or a combination of the materials. The anterior fixation blade 110 includes blade tips 135 that are designed to penetrate bone with a sharp tip feature and continue to a leading edge or cutting edge 140, similar to a sickle. The blade tips 135 positioned at the outer perimeter of an anterior fixation blade 110 diameter facilitate immediate bone engagement at initial deployment. The blades are attached to an axial alignment boss 145. The blades include cutting edge that spans the entire length of the blade from the boss to the tip for all sizes. The axial alignment boss 145 has a first end 150 and a second end 155. The first end 150 includes a cylindrical rotating alignment feature that includes one or more blade resistance/securing/locking feature 160 that couples to the cage 105 (discussed below). The first end 150 further includes a drive mechanism 152 or recess configured to engage a deployment instrument for rotating the anterior fixation blade 110 between a closed and open position. The drive mechanism may be a Hex, Hex-a-lobe, spline, double hex, Bristol, polydrive, torq-set, square, slotted, Phillips, etc. In a preferred embodiment, the drive mechanism 152 is a fine spline deploying mechanism, such as a 32× spline mechanism. The fine spline mechanism generates more torque than comparable hex features, which is preferable in combination with the ratchet teeth features of the present system 100. The second end 155 of the boss 145 includes an opening 165 configured to interact with the posterior fixation blade 115 and also allows insertion of the deployment instrument for actuation of the posterior fixation blade 115. The second end 155 of the boss 145 further includes ratchet teeth features 156 adapted to engage with ratchet pawl features 250 on the C-clip 245, when the system 100 is assembled. There is a tactile and audible feedback to the user when the pawl jumps over the ratchet teeth on the blades. In one embodiment, the ratchet teeth 156 have a 25 degree engagement angle 156a and a 10 degree back angle 156b. The back angle 156b prevents the ratchet teeth 156 from disengaging the ratchet pawl 250 of the C-clip 245, which would permit the blade 110 to collapse and back out from a deployed position. In some embodiments, the second end 155 of the boss 145 may also include dovetail features 157. The dovetail features 157 are designed to contact the dovetail features 260 on the C-clip 245, so as to retain the C-clip 245 in position and prevent the C-clip 245 from "popping out" or otherwise disengaging from the system 100 in the event that the blade 110 is over deployed. In another embodiment, the C-clip 245 may serve to limit the final angulation of the blade 110.

FIGS. 8A-8E show one embodiment of a posterior fixation blade 115 that includes curved blades designed to penetrate the end plates of adjacent vertebrae. Smooth curved or a series of straight sections that form the curved blades maximize graft volume and minimize graft displacement during deployment. The posterior fixation blade 115 may be constructed of titanium, a titanium alloy, polyetherketoneketone (PEEK), or any other biologically acceptable inert materials that would provide a rigid structure. The posterior fixation blade 115 may also be constructed with a combination of the materials. The posterior fixation blade 115 includes blade tips 170 that are designed to penetrate with a sharp tip feature and continue to a sharp leading edge or cutting edge 175, similar to a sickle. The blade tips 170 at the outer perimeter of the diameter facilitate immediate bone engagement at initial deployment. The blades are attached to an axial alignment boss 180. The blades include a cutting edge that spans the entire length of the blade from the boss to the tip for all sizes. The axial alignment boss 180 has a first end 185 and a second end 190. The first end 185 is designed to slidably fit within the opening 165 of the anterior fixation blade 110. The first end 185 further includes a drive mechanism 187 or recess for rotating the blade between a closed and open position. The drive mechanism may be a Hex, Hex-a-lobe, spline, double hex, Bristol, polydrive, torq-set, square, slotted, Phillips, etc. In a preferred embodiment, the drive mechanism 187 is a fine spline deploying mechanism, such as a 16× spline mechanism. The fine spline mechanism generates more torque than comparable hex features, which is preferable in combination with the ratchet teeth features of the present system 100. The second end 190 includes a cylindrical rotating alignment feature that includes one or more blade resistance/securing/locking feature 195 configured to couple with the cage 105. The second end 190 of the boss 180 further includes ratchet teeth features 181 adapted to engage with ratchet pawl features 250 on the C-clip 245, when the system 100 is assembled. There is a tactile and audible feedback to the user when the pawl jumps over the ratchet teeth on the blades. In one embodiment, the ratchet teeth 181 have a 25 degree engagement angle 181a and a 10 degree back angle 181b. The back angle 181b prevents the ratchet teeth 181 from disengaging the ratchet pawl 250 of the C-clip 245, which would permit the blade 115 to collapse and back out from a deployed position. In some embodiments, the second end 190 of the boss 180 may also include dovetail features 182. The dovetail features 182 are designed to contact the dovetail features 260 on the C-clip 245, so as to retain the C-clip 245 in position and prevent the C-clip 245 from "popping out" or otherwise disengaging from the system 100 in the event that the blade 115 is over deployed. In another embodiment, the C-clip 245 may serve to limit the final angulation of the blade 115.

FIGS. 9A-9F show different views and features of the cage 105. The cage 105 may be made of a rigid construction and preferably provided in several different sizes and shapes to fill differently sized evacuated spaces in differently sized individuals. The cage 105 has an interior opening 200 for storage of the blades 110, 115. The curves shape of the blades 110, 115 allow packing of bone graft material (see FIG. 3). The cage 105 may be constructed of a radiolucent material, such as polyetherketoneketone (PEEK), a commercially pure titanium, a titanium alloy or any other biologically acceptable inert materials that would provide the cage with a rigid structure.

The cage 105 is annular in configuration having an upper surface 205 and an opposed lower surface 210 configured to engage superiorly and inferiorly the end plates of adjacent vertebrae, and an annular side wall 215 around the hollow interior opening 200. The annular side wall 215 may have varying height, length, and thickness, and may include lordotic angle for better anatomical fit. In some embodiments, a plurality of outwardly projecting sharp raised ridges/teeth/striations 220 are formed on the surfaces 205, 210 for biting into and gripping the vertebral end plates (not shown). The ridges 220 may have a variable thickness, height, and width as well as an angle with respect to surfaces. The ridges 220 may be disposed at slightly offset angles with respect to each other or, alternatively with respect to the ridges on different portions of the cage, to reduce the possibility of the ridges sliding in any direction along the end plates and to prevent rotation of the cage on the end plate. For example, the figures show the ridges 220 on one side or portion of the surface 205 are all in parallel alignment, but misaligned with the ridges on the other side or portion. While it may be preferable that the ridges 220 are identical in configuration on the upper and lower surfaces, in some embodiments, the ridges or teeth different or have a different pattern for each surface.

Figure 9A:
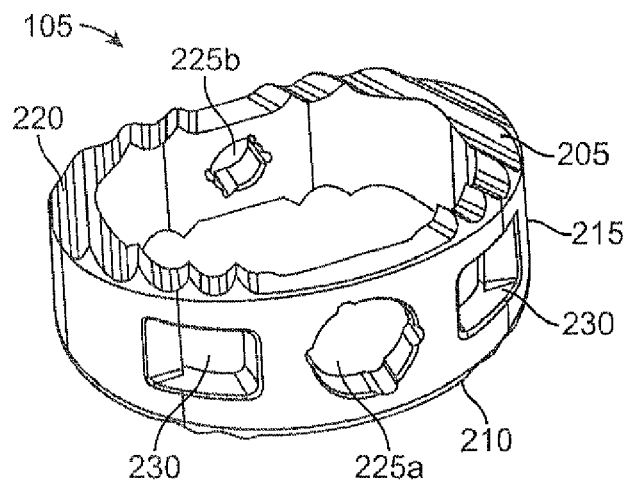
FIGS. 9A-F show different views and features of the cage of one embodiment of a stand-alone interbody fixation system having a ratchet teeth locking feature.
Figure 9B:
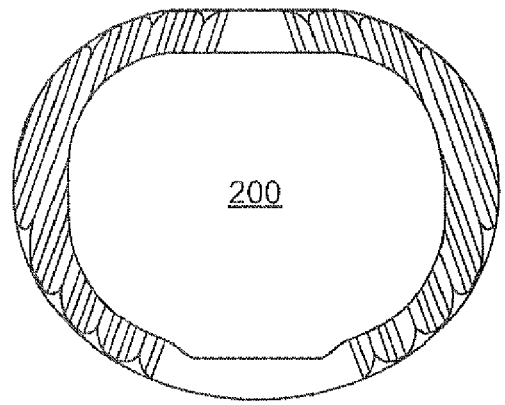
Figure 9C:
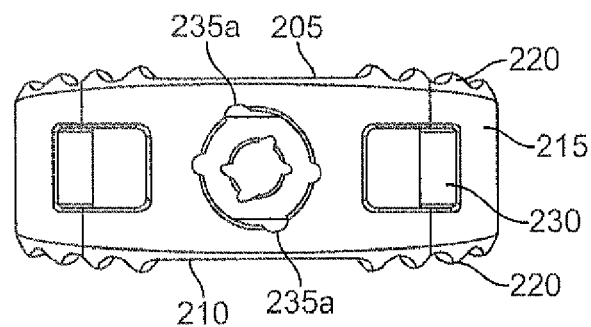
Figure 9D:
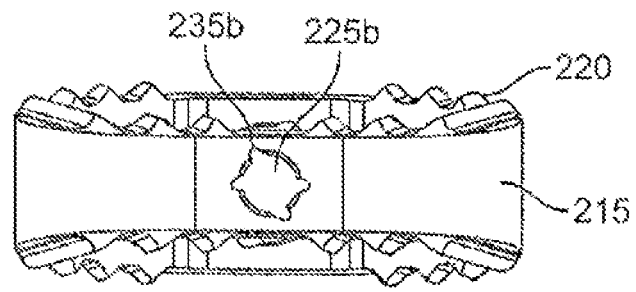
Figure 9E:
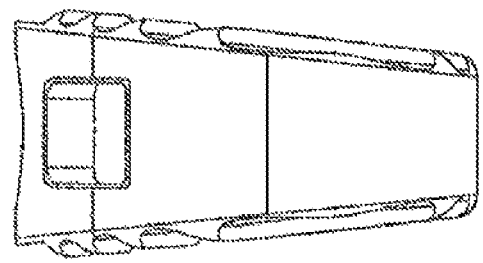
Figure 9F:
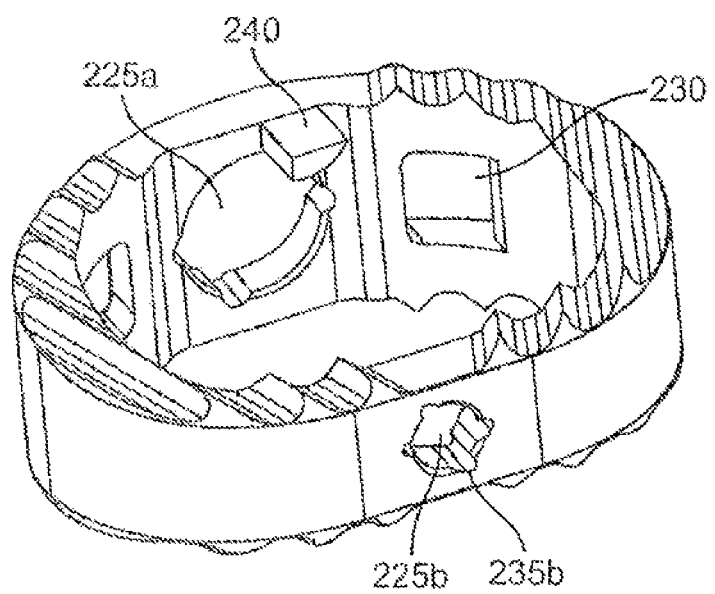

A plurality of openings 225, 230 are disposed in the side wall 215 of the cage 105. Opening 225a is configured to receive or engage end 150 of fixation blade 110 and opening 225b is configured to receive or engage end 190 of fixation blade 115. Other openings 230 spaced about the cage may be configured to receive or engage an insertion tool or deployment instrument (not shown), or used to pack bone or other suitable bone graft material. Openings 225a, 225b are generally circular in shape and include blade resistance/locking features 235a, 235b to hold blades in one or more positions. These features 235a, 235b may include grooves, notches or dimples that couple or interact with ridges, tabs or bumps 160, 195 on blades 110, 115. When end 150 of fixation blade 110 is inserted into opening 225a, bumps 160 interact with one of the grooves 235a. As the blade is rotated, the bumps 160 may move from one set of grooves 235a in a stored position to another set of grooves 235a in the deployed position, to form a locking mechanism. When end 190 of fixation blade 115 is inserted into opening 225b, bumps 195 interact with one of the grooves 235b. As the blade is rotated, the bumps 195 may move from one set of grooves 235b in a stored position to another set of grooves 235a in the deployed position, to form a locking mechanism. Openings 230 may be generally rectangular in shape to accommodate an insertion tool or deployment instrument having a center blade activation portion disposed between a pair of prongs, so that the tool can grip the openings 230 of the cage and/or rotate the blades. As shown in FIG. 9F, a blade stopping feature 240 may also be used to contact the blades and prevent the blades from rotating more than a desired angle.

Figure 10A:
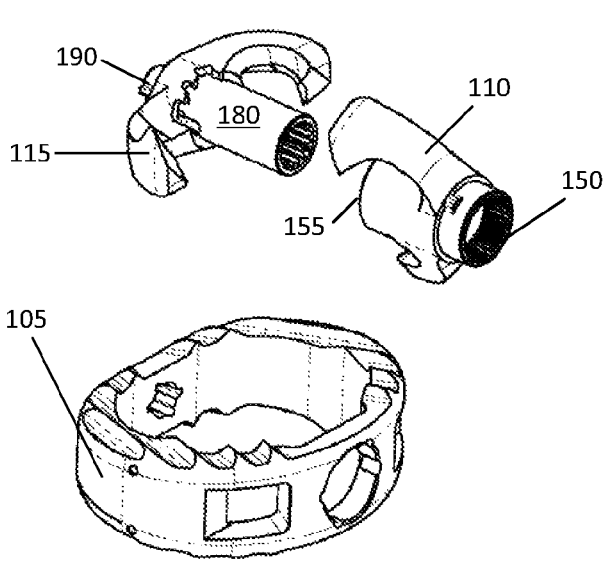
FIGS. 10A-K show one example of an assembly method for an embodiment of the present system.
Figure 10B:
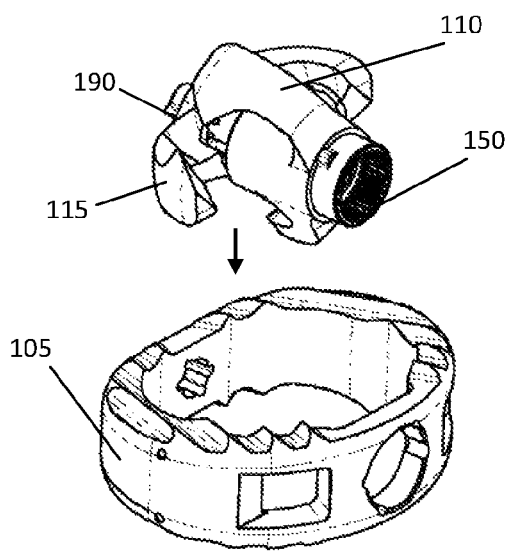
Figure 10C:
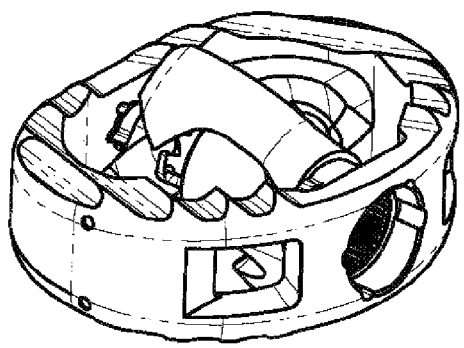
Figure 10D:
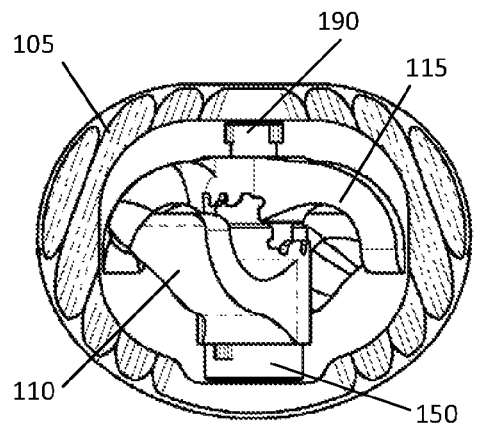
Figure 10E:
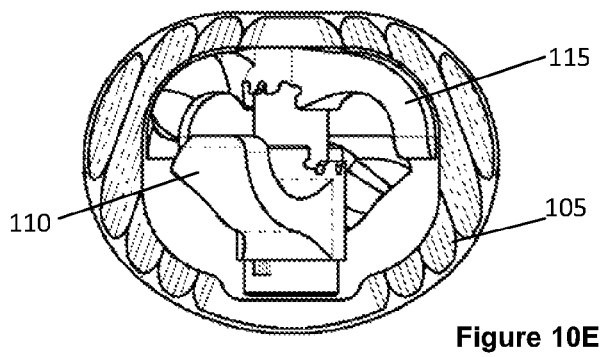
Figure 10F:
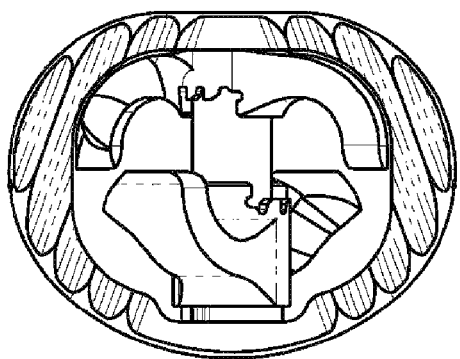
Figure 10G:
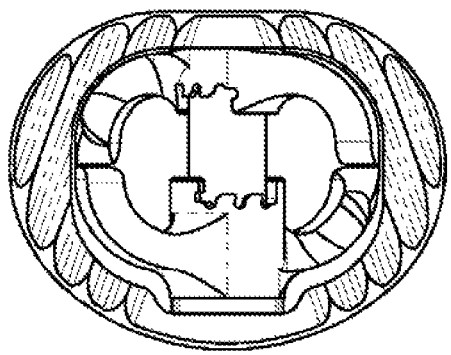
Figure 10H:
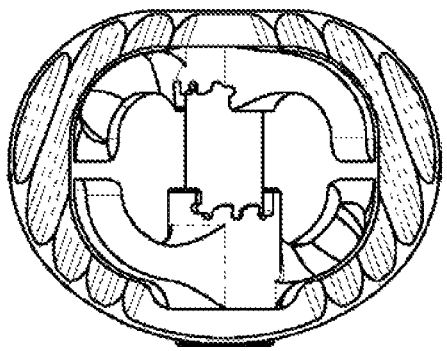
Figure 10I:
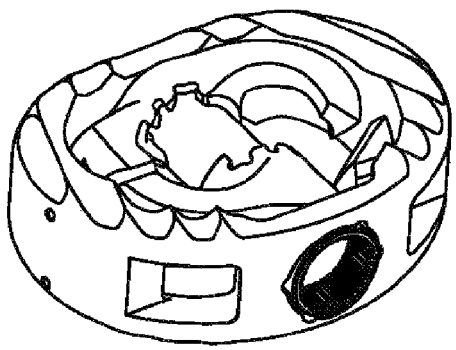
Figure 10J:
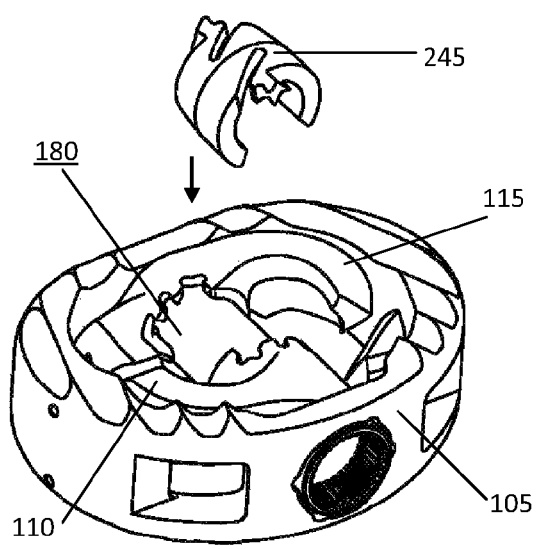
Figure 10K:
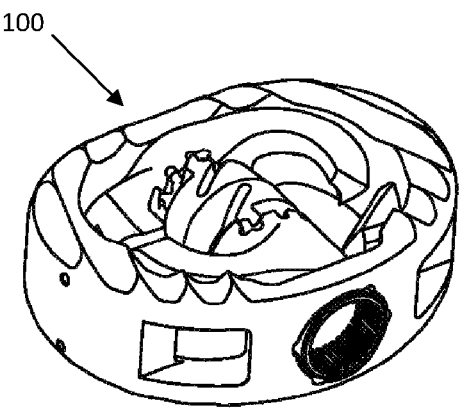

FIGS. 10A-10K show one example of an assembly method for system 100. The anterior fixation blade 110 and posterior fixation blade 115 are aligned (FIG. 10A) and the first end 185 of the posterior fixation blade 115 is inserted into the opening 160 near the second end 155 of the anterior fixation blade 110. When fully inserted, the distance between the first end 150 of the anterior fixation blade 110 and the second end 190 of the posterior fixation blade 115 is less than an interior distance between the first opening 225a and second opening 225b of the cage 105 (FIG. 10B). With the blades 110, 115 combined in this manner, they may be inserted into the central opening 200 and positioned within the cage 105 (FIGS. 10C, 10D). The blades 110, 115 may then be moved or extended in opposite directions until the first end 150 of the anterior fixation blade 110 is inserted into the first opening 225a and the second end 190 of the posterior fixation blade 115 is inserted into the second opening 225b and the blades are rotated to the stored position (FIGS. 10E-10I). To keep the blades 110, 115 in the extended position, the C-clip 245 is slid over the boss 180 of the posterior fixation blade 115 (FIG. 10J) to keep the ends of the anterior and posterior fixation blades 110, 115 within the openings 225a, 225b forming the system 100 (FIG. 10K). The ratchet teeth features 250 of the C-clip 245 engage with the ratchet teeth features 156 of the anterior blade 110 and the ratchet teeth features 181 of the posterior blade 115. This engagement of the ratchet teeth features 250, 156, 181 prevents collapse of deployed blades 110, 115, when either fully deployed or partially deployed.

Example embodiments of the methods and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed is:

1. A stand-alone interbody fixation system comprising:
   a. a cage having an annular side wall with an open interior and upper and lower surfaces, the cage being configured to fit between end plates of adjacent vertebrae;
   b. an anterior fixation blade having an anterior alignment boss with two opposing outward extending anterior blades with end plate penetrating tips configured to fit within the open interior of the cage, the anterior alignment boss having first and second ends, the first end of the anterior alignment boss being rotatably coupled with a first opening in the annular side wall, wherein the anterior alignment boss further comprises ratchet teeth;
   c. a posterior fixation blade having a posterior alignment boss with two opposing outward extending posterior blades with end plate penetrating tips configured to fit within the open interior of the cage, the posterior alignment boss having first and second ends, the first end being rotatably coupled to the second end of the anterior alignment boss and the second end of the posterior alignment boss being rotatably coupled with a second opening in the annular side wall opposite the first opening, wherein the posterior alignment boss further comprises ratchet teeth; and d. a C-clip positioned between the anterior and posterior fixation blades configured to keep the anterior and posterior fixation blades in the fixation blade retention position in the cage, the C-clip further comprises at least two ratchet pawls, each adapted to engage the ratchet teeth of one of the anterior or posterior alignment bosses;

e. wherein the anterior and posterior fixation blades are counter-rotating and the engagement of the ratchet pawls of the C-clip with the ratchet teeth of the anterior and posterior alignment bosses prevents the anterior and posterior fixation blades from collapsing from a full or partially deployed state to a stowed state.

2. The system of claim 1, wherein the anterior and posterior blades further include a cutting edge between the boss and tip.

3. The system of claim 1, wherein the anterior and posterior blades are curved blades.

4. The system of claim 3, wherein the curved blades are shaped to follow the annular side wall within the open interior.

5. The system of claim 1, wherein the anterior and posterior blades may be constructed of titanium, a titanium alloy, polyetherketoneketone (PEEK), or any other biologically acceptable materials, or a combination of the materials, capable of penetrating the end plate.

6. The system of claim 1, wherein when coupled, the anterior and posterior fixation blades are movable from a fixation blade insertion position for positioning the coupled anterior and posterior blades in the cage to a fixation blade retention position in which the coupled anterior and posterior fixation blades are moved apart and the first end of the anterior alignment boss is within the first opening in the annular side wall and the second end of the posterior alignment boss is within the second opening in the annular side wall.

7. The system of claim 1, wherein the ratchet pawls of the C-clip each further comprise a slot spring mechanism.

8. The system of claim 1, wherein the first and second openings in the annular side wall include grooves and the first end of the anterior boss and the second end of the posterior boss include bumps, the bumps configured to interact with the grooves and hold the anterior and posterior fixation blades in one or more positions.

9. The system of claim 1, wherein the upper and lower surface include outwardly projecting sharp raised ridges, teeth and/or striations.

10. The system of claim 1, wherein the anterior alignment boss and posterior alignment boss further comprise a fine spline deploying mechanism.

11. The system of claim 1, wherein the anterior alignment boss, the posterior alignment boss, and the C-clip each further comprise a dovetail element, adapted to retain the C-clip and prevent the C-clip from disengaging if the anterior or posterior blades are over deployed.

12. The system of claim 1, wherein the C-clip limits the final angulation between the anterior and posterior fixation blades.

13. A stand-alone interbody fixation system comprising:

a. a cage having an annular side wall with an open interior and upper and lower surfaces having outwardly projecting sharp raised ridges, teeth and/or striations, the cage being configured to fit between end plates of adjacent vertebrae;

b. an anterior fixation blade having an anterior alignment boss with two curved opposing outward extending anterior blades shaped to follow the annular side wall within the open interior, the blades being capable of penetrating the end plate, the anterior alignment boss being rotatably coupled to a first opening in the annular side wall, wherein the anterior alignment boss further comprises ratchet teeth;

c. a posterior fixation blade having a posterior alignment boss with two curved opposing outward extending posterior blades shaped to follow the annular side wall within the open interior, the blades being capable of penetrating the end plate, the posterior alignment boss being rotatably coupled to the anterior alignment boss and further rotatably coupled with a second opening in the annular side wall opposite the first opening, wherein the posterior alignment boss further comprises ratchet teeth; and d. a C-clip positioned between the anterior and posterior fixation blades configured to keep the anterior and posterior fixation blades in the fixation blade retention position in the cage, the C-clip further comprises at least two ratchet pawls, each adapted to engage the ratchet teeth of one of the anterior or posterior alignment bosses;

e. wherein the anterior and posterior fixation blades are counter-rotating blades, and the ratchet pawls of the C-clip progressively engage with the ratchet teeth of the anterior and posterior alignment bosses as the fixation blades advance from a stowed position to partially or fully deployed positions, and the C-clip prevents the anterior and posterior fixation blades from collapsing from the partially or fully deployed positions to the stowed position.

14. The system of claim 13, wherein the anterior and posterior blades further include end plate penetrating tips.

15. The system of claim 13, wherein the first and second openings in the annular side wall include grooves and the anterior alignment boss and the posterior alignment boss include bumps, the bumps configured to interact with the grooves and hold the anterior and posterior fixation blades in one or more positions.

16. The system of claim 13, wherein the anterior and posterior blades may be constructed of titanium, a titanium alloy, polyetherketoneketone (PEEK), or any other biologically acceptable materials, or a combination of the materials, capable of penetrating the end plates.

17. The system of claim 13, wherein the anterior alignment boss, the posterior alignment boss, and the C-clip each further comprise a dovetail element, adapted to retain the C-clip and prevent the C-clip from disengaging if the anterior or posterior blades are over deployed.

18. The system of claim 13, wherein the ratchet pawls of the C-clip each further comprise a slot spring mechanism.

19. The system of claim 13, wherein the C-clip limits the final angulation between the anterior and posterior fixation blades 1.

* * * * *